US012779094B2

(12) United States Patent
Velasco et al.

(10) Patent No.: US 12,779,094 B2
(45) Date of Patent: Nov. 3, 2026

(54) METHODS OF TREATING CARTILAGE WITH PSEUDOPLASTIC HYDROLYZED COLLAGEN-CONTAINING COMPOSITIONS

(71) Applicant: ROCHAL TECHNOLOGIES LLC, San Antonio, TX (US)

(72) Inventors: Jonathan Velasco, San Antonio, TX (US); Ann Beal Salamone, Gainesville, FL (US); Rebecca McMahon, San Antonio, TX (US); Nina Bionda, Ithaca, NY (US); Fahimeh Tabatabaei, Boerne, TX (US); Fawn Sanchez, Helotes, TX (US); Sergio Medina, San Antonio, TX (US)

(73) Assignee: ROCHAL TECHNOLOGIES LLC, San Antonio, TX (US)

( * ) Notice: Subject to any disclaimer, the term of this patent is extended or adjusted under 35 U.S.C. 154(b) by 0 days.

(21) Appl. No.: 19/312,778

(22) Filed: Aug. 28, 2025

(65) Prior Publication Data

US 2026/0061100 A1 Mar. 5, 2026

Related U.S. Application Data

(60) Provisional application No. 63/716,769, filed on Nov. 6, 2024, provisional application No. 63/688,129, filed on Aug. 28, 2024.

(51) Int. Cl.

| | |
|---|---|
| ***A61L 27/52*** | (2006.01) |
| ***A61K 9/06*** | (2006.01) |
| ***A61K 47/42*** | (2017.01) |
| ***A61L 27/26*** | (2006.01) |
| ***A61L 27/54*** | (2006.01) |
| ***C08L 71/02*** | (2006.01) |
| ***C08L 89/06*** | (2006.01) |

(52) U.S. Cl.

CPC ................ *A61L 27/52* (2013.01); *A61K 9/06* (2013.01); *A61K 47/42* (2013.01); *A61L 27/26* (2013.01); *A61L 27/54* (2013.01); *C08L 71/02* (2013.01); *C08L 89/06* (2013.01); *A61L 2430/06* (2013.01); *C08L 2312/00* (2013.01)

(58) Field of Classification Search

CPC ....... A61L 27/52; A61L 27/54; A61L 2430/06

See application file for complete search history.

(56) References Cited

U.S. PATENT DOCUMENTS

| | | | | |
|---|---|---|---|---|
| 5,807,581 | A | 9/1998 | Rosenblatt | |
| 6,025,327 | A * | 2/2000 | Alkayali | C07K 14/78 530/356 |
| 11,590,259 | B2 | 2/2023 | Salamone | |
| 2009/0226519 | A1 | 9/2009 | Claude | |
| 2016/0303281 | A1 * | 10/2016 | Salamone | A61L 27/18 |
| 2018/0256641 | A1 | 9/2018 | Attar | |
| 2023/0083186 | A1 | 3/2023 | DeVore | |

OTHER PUBLICATIONS

Karim, A., et al., "The clustering and morphology of chondrocytes in normal and mildly degenerate human femoral head cartilage studied by confocal laser scanning microscopy," J. Anat. (2018) 232, pp. 686-698.

* cited by examiner

*Primary Examiner* — Andrew S Rosenthal

(74) *Attorney, Agent, or Firm* — DUANE MORRIS LLP; Gregory M. Lefkowitz; Brandon A. Chan

(57) ABSTRACT

A method to treat cartilage and peri-cartilage is provided which utilizes a pseudoplastic scaffold comprising a PEGylated protein-containing microgel and a hydrolyzed collagen component. The pseudoplastic scaffold composition can be applied topically, via injection, or via ingestion.

19 Claims, 2 Drawing Sheets

A

B

C

D

METHODS OF TREATING CARTILAGE WITH PSEUDOPLASTIC HYDROLYZED COLLAGEN-CONTAINING COMPOSITIONS

CROSS-REFERENCE TO RELATED APPLICATIONS

This application claims priority to U.S. Application Ser. No. 63/688,129, filed Aug. 28, 2024, and U.S. Application Ser. No. 63/716,769, filed Nov. 6, 2024, the entireties of which are incorporated herein by reference.

FIELD OF INVENTION

This invention relates generally to methods for the treatment of cartilage and peri-cartilage. In particular, using a pseudoplastic scaffold comprising a crosslinked PEGylated protein-containing microgel and a hydrolyzed collagen component in order to enhance cartilage and peri-cartilage cell viability and extracellular matrix integrity.

BACKGROUND

Cartilage is connective tissue that protects joints and bones. It is found in the joints, spine, ribs, neck, bronchial tubes, trachea, ears and nose, for example, of vertebrates. Three types of cartilage exist which vary in function and composition; however, they all are avascular, alymphatic, and aneural. Transport of nutrients and waste is via diffusion to and from adjacent tissues (e.g., bone) and fluids (e.g., synovial fluid). Cartilage is composed of different layers, each serving specific functions including diffusion membranes. Thus, changes in composition related to impaired cartilage impact diffusion and thus, enable certain molecules (e.g., inflammatory proteins, vascular materials) to penetrate through cartilage tissue while detrimentally enabling excessive flow of peptides and proteins out of cartilage.

Peri-cartilage is defined as biological matter integrally connected to cartilage, for example, subchondral bone and perichondrium.

Damage to cartilage and perichondrium can be painful and even debilitating. A wide range of techniques and compositions have been developed to help maintain and heal cartilage, ameliorate the associated pain, or both.

BRIEF DESCRIPTION OF DRAWINGS

FIG. 2B shows that the cast film of FIG. 2A can be folded, FIG. 2C shows that the cast film of FIG. 2A can be crimped, and FIG. 2D shows that after 2 hours soaking in water, the cast film has swelled but remains insoluble.

SUMMARY OF THE INVENTION

The method of treating cartilage and pen-cartilage is described where cartilage and/or peri-cartilage is contacted with a pseudoplastic scaffold that includes a combination of hydrolyzed collagen and a PEGylated protein-containing microgel, comprising a protein component crosslinked by a PEGylating component. The pseudoplastic scaffold is pseudoplastic in aqueous media. The pseudoplastic scaffold can be coated, injected, sprayed, painted, or implanted onto or into cartilage and/or peri-cartilage as well as used to surround tissue replacement products. The pseudoplastic scaffolds including microgel particles and interpenetrating hydrolyzed collagen can function as a matrix to synergistically support cell viability, motility, and proliferation.

Figure 2:
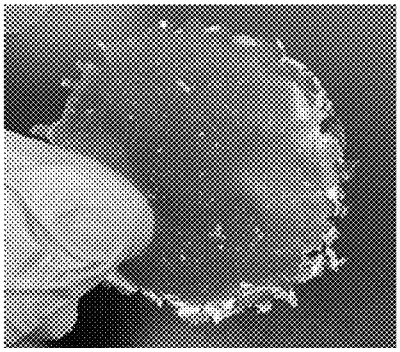
FIG. 2 shows a film cast from an aqueous scaffold of PEGylated microgel with hydrolyzed collagen.
Figure 2:
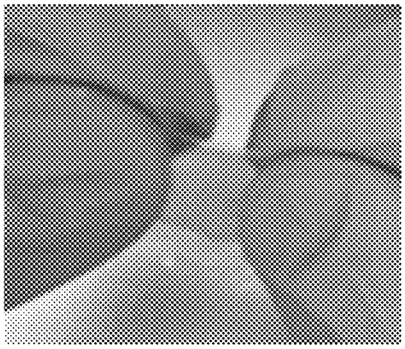
Figure 2:
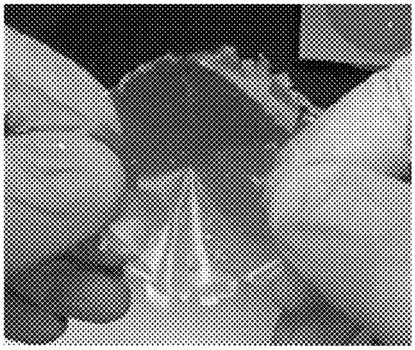
Figure 2:
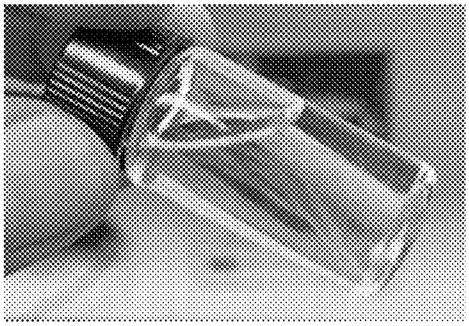

Water-insoluble, but water-swellable and deformable, crosslinked PEGylated microgel particles of protein-based macromolecules (microgel particles) are described which when mixed with hydrolyzed collagen powder form free-flowing compositions. Surprisingly, in aqueous media, the combination of microgel particles and hydrolyzed collagen form a flowable, pseudoplastic, non-stringy hydrogel that flows under application of shear and reforms into a solid gel upon removal of shear. As shown in FIGS. 2B and 2C, upon drying, these PEGylated gels form a flexible, continuous film which can be folded and crimped. As shown in FIG. 2D, the film is not water soluble but does swell when exposed to water or aqueous media. In contrast, microgel particles without the hydrolyzed collagen form discreet microgels in aqueous media which under shear, flow and upon removal of shear, reform as a cluster of microgel particles which cannot form a continuous film upon drying. Hydrolyzed collagen, in the absence of microgel particles, is readily water soluble.

In the pseudoplastic scaffolds described herein, the hydrolyzed collagen and PEGylated protein-containing microgel interact to form a water-insoluble, yet pseudoplastic hydrogel—an interpenetrating network—which is surprising given that both PEG and hydrolyzed collagen are above their isoelectric point at normal physiological pH of 5.5-7.

In some embodiments, the hydrolyzed collagen component is present when the PEGylated protein-containing microgel is formed whereby the protein component is crosslinked by a PEGylating component to form a PEGylated PHC-containing microgel (where "PHC" stands for protein+hydrolyzed collagen). In other embodiments, the PEGylated protein-containing microgel is formed and then mixed with the hydrolyzed collagen to form a "PEGylated microgel network." It has been surprisingly discovered that (1) both of these PEGylated compositions exhibit properties that are similar, and improved relative to either the PEGylated protein containing microgel alone or the hydrolyzed collagen alone; and (2) both unexpectedly provide improved cell viability. As used herein, the terms "PEGylated composition" and "pseudoplastic scaffold" are intended to reference both PEGylated microgel networks (which include hydrolyzed collagen) and PEGylated PHC-containing microgels.

While not necessary for practicing the invention, it is believed that in both pseudoplastic scaffolds, the interaction of hydrophilic, negatively charged PEG on the outer surface of the hydrated PEGylated protein-containing microgel particles with the hydrophilic, negatively charged hydrolyzed collagen is derived significantly from physical (as opposed to chemical) crosslinking. Hydrolyzed collagen is primarily composed of oligomers of glycine, proline, and hydroxyproline. Hydrolyzed collagen's amide components have delocalized electrons over the HN—C—O covalent bonds. This resonance allows the lone pair electrons on oxygen, found within the C—O—C ether unit of polyethylene glycol (PEG), to create a hydrogen bond with the amide hydrogen, which then drives entanglement or interpenetration of hydrolyzed collagen in the PEG layer of the microgel. Thus, it is believed that hydrogen bonding enhances entanglement between the hydrolyzed collagen component and the PEGylated protein-containing microgel regardless of which form of pseudoplastic scaffold is present.

Regardless of the mechanism, it has been determined that pseudoplastic scaffolds are water-insoluble hydrogels that are shear thinning but return to a solid hydrogel state when shear is removed.

Further, when hydrolyzed collagen is present during PEGylation (crosslinking) of the protein-based macromolecule to form a PEGylated PHC-containing microgel, the hydrolyzed collagen is likely also PEGylated to a lesser extent and thus, a portion of the hydrolyzed collagen is chemically crosslinked as well as physically crosslinked within the composition.

The pseudoplastic scaffolds described herein can be utilized in their powder state and can be placed into or on a cartilage defect, a peri-cartilage defect, or surrounding such a defect or a tissue replacement product, wherein the powder mixture can be hydrated by endogenous or exogenous sources.

Depending on the type of injured or compromised cartilage or peri-cartilage or impaired tissue parameters (e.g., location, cause, size, depth) the pseudoplastic scaffold can be formulated into a powder, a hydrogel format, or a film format and applied to or proximate a cartilage or peri-cartilage defect.

Examples of injured or compromised tissue include, but are not limited to, immune response tissue damage, lesions, fissures, aging or disease, such as cancer or osteoarthritis. The tissue can be injured or compromised physiologically or as the result of infection, surgery, cyst, tumor removal, or traumatic injury or remodeling of tissue, such as in plastic surgery, cosmetic surgery, reconstructive surgery, coating/sealing of tissue replacement products, tendon repair, hernia repair, craniofacial surgery, ophthalmic surgery, cervicofacial rhytidectomy, cartilage repair, nerve repair, spinal cord repair, rheumatology, body contouring, and the like.

Tissue replacement utilizing tissue engineered cartilage replacement products and spray-on cells is used to provide tissue repair for difficult-to-heal defects, including cartilage and pen-cartilage repair. Non-incorporation of the tissue replacement product and infection can be key determinants for lack of success in healing when using tissue replacement products. Tissue replacement products often fill approximately 60% of the defect, leaving approximately 40% of the defect area without continuous contact for cell motility as well as open areas for desiccation/maceration and infection development. The pseudoplastic scaffolds described herein form a coating that is conformable to surrounding tissues, filling defect void space whether applied as hydrated gel or as a powder and hydrated in situ. Once hydrated, the hydrated gel enhances cell motility between tissue replacement products and the defect bed, decreasing desiccation and maceration. When an antimicrobial agent is added to the pseudoplastic scaffold, infection can be reduced or eliminated, thereby improving healing effectiveness.

In some embodiments, the disclosure provides a method for treatment of cartilage and peri-cartilage utilizing a pseudoplastic scaffold comprising hydrolyzed collagen and crosslinked, water-swellable microgel particles of protein-based macromolecules (PEGylated protein-containing microgel) to treat cartilage and peri-cartilage. In some embodiments, the method utilizing the pseudoplastic scaffold is a PEGylated microgel network, while the PEGylated pseudoplastic scaffold is a PEGylated PHC-containing microgel in other embodiments.

In some embodiments, the disclosure provides for a method for treatment of cartilage and peri-cartilage, wherein the hydrolyzed collagen is mixed with microgel particles of protein-based macromolecules that are crosslinked by a difunctional to multifunctional PEGylating components.

In some embodiments, the disclosure provides a method for treatment of cartilage and peri-cartilage wherein the pseudoplastic scaffold can be hydrated with aqueous media.

In some embodiments, the disclosure provides a method for treatment of cartilage and peri-cartilage wherein the hydrated scaffold particles are pseudoplastic under shear in aqueous media.

In some embodiments, the disclosure provides for a method to treat cartilage and peri-cartilage with a pseudoplastic scaffold in aqueous media where, when shear is removed from the hydrated mixture, a hydrogel forms.

In some embodiments, the disclosure provides a method to treat cartilage and peri-cartilage where a pseudoplastic scaffold can be coated, injected, sprayed, painted, or implanted in, on, or proximate to cartilage and/or peri-cartilage, tissue replacement products, bandages, and medical devices.

In some embodiments, the disclosure provides methods to treat cartilage and peri-cartilage with the pseudoplastic scaffold described herein.

In some embodiments, the disclosure provides for a method to treat cartilage and peri-cartilage with the pseudoplastic scaffold which is a component of nutraceuticals or pharmaceuticals.

In some embodiments, the method to treat cartilage and pen-cartilage provides for inclusion of biologically active agents into the pseudoplastic scaffolds described herein.

In some embodiments, the biologically active agents are cells.

In some embodiments, the cells are of human origin and are either autologous or allogeneic.

In some embodiments, the cells are stem cells of human origin and are either autologous or allogeneic.

In some embodiments, the biologically active agent is decellularized extracellular matrix derived from stem cells.

In some embodiments, the biologically active agent is micronized or morselized tissue, such as, but not limited to, spinal cord, bladder, small intestinal submucosa, cartilage, placenta, extracellular matrix, tendon, umbilical cord, cornea, heart, myocardium, muscle, and combinations thereof.

In some embodiments, the biologically active agent is morselized amniotic tissue.

In some embodiments, the biologically active agent is minced tissue.

In some embodiments, the biologically active agent is micronized tissue.

In some embodiments, the biologically active agent is granulated crosslinked bovine tendon collagen and/or glycosaminoglycan.

In some embodiments, the biologically active agent is amniotic fluid.

In some embodiments, the biologically active agent is Wharton's jelly.

In some embodiments, the biologically active agent is micronized cartilage tissue.

In some embodiments, the biologically active agent is a drug.

In some embodiments, the biologically active agent has antimicrobial properties.

In some embodiments, the method to treat cartilage and peri-cartilage where water-soluble polymers are included with the pseudoplastic scaffold.

In some embodiments, the method to treat cartilage and peri-cartilage wherein the pseudoplastic scaffold can be applied as a powder, liquid, gel, paste, cream, emulsion, film, sheet, or combinations thereof.

DETAILED DESCRIPTION OF THE INVENTION

In this specification and the appended claims that follow, reference will be made to a number of terms that shall be defined to have the following meanings:

It must be noted that, as used in the specification and the appended claims, the singular forms “a”, “an” and “the” include plural references unless the context clearly dictates otherwise. Thus, for example, reference to “a surfactant” includes mixtures of two or more such surfactants, and the like.

As used herein, the term “about” indicates that a value can vary by up to ±5%, ±2%, or ±1%.

In some aspects, a method to treat cartilage and pen-cartilage is by applying a pseudoplastic scaffold to the cartilage and pen-cartilage, where the pseudoplastic scaffold includes a PEGylated protein-containing microgel, comprising a protein component crosslinked by a PEGylating component; and a hydrolyzed collagen component.

Figure 3:
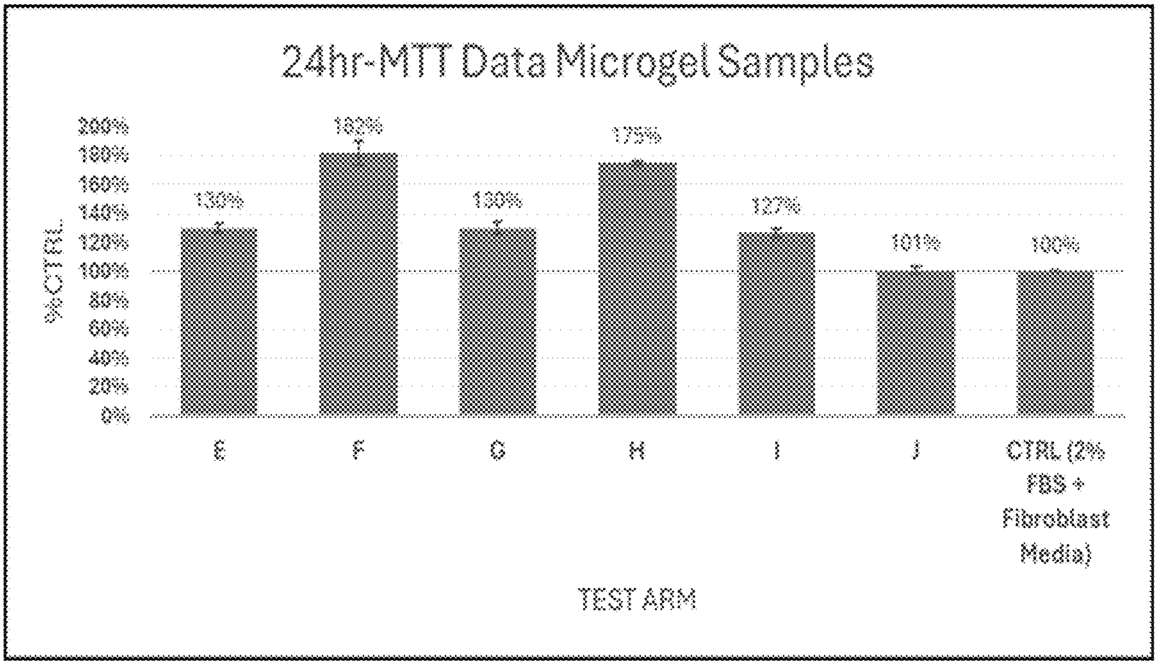
FIG. 3 shows MTT data for pseudoplastic scaffold containing hydrolyzed collagen, PEGylated protein-containing microgels, or combinations of both.

Surprisingly, these pseudoplastic scaffolds synergistically improve cell viability, metabolic activity, and/or proliferation as demonstrated by MTT assay results to measure cellular metabolic activity. Individually, hydrated hydrolyzed collagen and hydrated gelatin, a protein used in the microgel synthesis, increase metabolic activity to above the control. However, pseudoplastic scaffolds described herein, which contain both PEGylated protein-containing microgel and a hydrolyzed collagen component, demonstrate a 75% to 82% increase above control. This is shown in FIG. 3. AlamarBlue results further confirm enhanced cell viability with cartilage tissue.

Further, extracellular matrix component generation is improved as demonstrated through GAG quantification using dimethylmethylene blue (DMMB) assay.

While not necessary to practice the invention, it is believed that a portion of the hydrolyzed collagen component may be covalently or non-covalently (e.g., H-bonding) bound to the PEGylated protein-containing microgel. In either case, free hydrolyzed collagen is burst released in aqueous media while hydrolyzed collagen bound to the PEGylated protein-containing microgel is biologically degraded over days in the presence of body fluids. Hydrolyzed collagen stimulates production of inflammatory macrophage, M1. Thus, the burst release of hydrolyzed collagen enables early inflammation to rid the body of foreign debris, such as microbes, and necrotic tissue. The enduring composition of bound hydrolyzed collagen to microgel provides a pseudoplastic substrate for cell proliferation, stimulates endothelial proliferation for vascular development, and stimulates the production of anti-inflammatory macrophage, M2, for tissue repair.

In some embodiments, the molar ratio of the hydrolyzed collagen component to the protein component is at least 1:1. In some embodiments, the molar ratio of the hydrolyzed collagen component to the protein component is at least 2:1, or at least 3:1, or at least 5:1, or at least 8:1, or at least 10:1.

In some embodiments, the molar ratio of the hydrolyzed collagen component to the protein component is not more than 100:1. In some embodiments, the molar ratio of the hydrolyzed collagen component to the protein component is not more than 75:1, or not more than 50:1, or not more than 40:1.

In some embodiments, the hydrolyzed collagen component is present during the reaction where the protein component is crosslinked by the PEGylating component, and the PEGylated protein-containing microgel is a PEGylated PHC-containing microgel. In such instances, the hydrolyzed collagen component may be crosslinked by the PEGylating component. Regardless of whether the hydrolyzed collagen component is crosslinked by the PEGylating component, it is believed that the hydrolyzed collagen component is more entangled within PEGylated protein-containing microgel. Regardless, in such embodiments, the PEGylated protein-containing microgel comprises the hydrolyzed collagen component.

In some embodiments, the hydrolyzed collagen component is not crosslinked by the PEGylating component. In such embodiments, the hydrolyzed collagen is not present when the protein component is crosslinked by the PEGylating component. In some embodiments, the PEGylated composition is two discrete powders that can be hydrated to form a PEGylated microgel network. In some embodiments, the hydrolyzed collagen component and the PEGylated protein-containing microgel have been solubilized in a liquid carrier to form a PEGylated microgel network.

In embodiments, a molar ratio of the PEGylating component to the protein component is at least 5:1. In some such embodiments, a molar ratio of the PEGylating component to the protein component is at least 8:1, or at least 10:1.

In embodiments, a molar ratio of the PEGylating component to the hydrolyzed collagen component is at least 0.2:1 (i.e., a 10:50 ratio). In some embodiments, a molar ratio of the PEGylating component to the hydrolyzed collagen component is at least 0.25:1, or at least 0.33:1, or at least 0.4:1, or at least 0.5:1, or at least 1:1. In some embodiments, a molar ratio of the PEGylating component to the hydrolyzed collagen component is less than 10:1, or less than 5:1, or less than 2.5:1.

In some embodiments, the PEGylated composition comprises 5 to 99 mole parts of the hydrolyzed collagen component; and 1 to 95 mole parts of the PEGylated protein-containing microgel.

In some embodiments, the PEGylated composition comprises 8 to 82 mole parts of the hydrolyzed collagen component; and 18 to 92 mole parts of the PEGylated protein-containing microgel.

In some embodiments, the PEGylated composition comprises 8 to 63 mole parts of the hydrolyzed collagen component; and 37 to 92 mole parts of the PEGylated protein-containing microgel.

In some embodiments, the PEGylated composition is non-stringy and pseudoplastic in aqueous media. In some embodiments, such compositions range from 5 mol % to 99 mol % of hydrolyzed collagen and 1 mol % to 95 mol % microgel.

In some embodiments, the hydrolyzed collagen component is derived from bovine, porcine, ovine, avian, marine, mixed sources, or other sources. Hydrolyzed collagen is generally considered to have a molecular weight range of 75 Da to 12,000 Da and is composed of lower molecular weight peptides, oligopeptides, and amino acids. The composition and molecular weight range varies depending on hydrolysis method (acid, alkaline, enzymatic) and processing technique. Hydrolyzed collagen is highly water soluble and is not viscous when dissolved in water until about 60 wt % in water where a water-soluble gel is formed. When dried, this hydrolyzed collagen gel forms a brittle coating that is readily water soluble. For the sake of clarity, it is noted that consistent with its standard meaning, hydrolyzed collagen is not a protein.

In some embodiments, the PEGylated protein-containing microgel particles are comprised of PEG-crosslinked protein-based macromolecules which have been lyophilized and milled to form dry microgel particles. In some embodiments, the particles absorb at least 2 times their dry weight of saline, or at least 5 times, or at least 10 times, or at least 20 times, or at least 30 times, or at least 40 times, or at least 50 times their dry weight of saline. In some embodiments, the particles have a dried particle size of 5.3 μm to 1,832.8 μm in length and 1.6 μm to 894.2 μm in width.

In some embodiment, the protein component is or comprises gelatin, and the gelatin is crosslinked with the PEGylating component to form microgel particles. Gelatin can be derived from bovine, porcine, ovine, avian, piscine, or mixed sources. The molecular weight of the gelatin as provided in Bloom numbers may range, in general, from 150 to 275. However, this range is for demonstration only and may be a wider range (Bloom range from 30 to 325).

In some embodiments, the PEGylating component is selected from α-aminopropyl-ω-aminopropoxypolyoxyethylene, α-aminopropyl-ω-carboxypentyloxypolyoxyethylene, α,ω-bis{2-[(3-carboxy-1-oxopropyl)amino]ethyl}polyethylene glycol, α-[3-(3-maleimido-1-oxopropyl)amino]propyl-ω-[3-(3-maleimido-1-oxopropyl)amino]propoxypolyoxyethylene, pentaerythritol tetra(aminopropyl)polyoxyethylene, α-[3-(3-maleimido-1-oxopropyl)amino]propyl-ω-(succinimidyloxycarboxy)polyoxyethylene, pentaerythritol tetra(succinimidyloxyglutaryl)polyoxyethylene, pentaerythritol tetra(mercaptoethyl)polyoxyethylene, hexaglycerol octa(succinimidyloxyglutaryl)polyoxyethylene, hexaglycerol octa(4-nitrophenoxycarbonyl)polyoxyethylene, 4-arm poly(ethylene glycol) tetraacrylate, 4-arm succinimidyloxyglutaryl)polyoxyethylene, bis(polyoxyethylene bis[imidazoyl carbonyl]), O-(3-carboxypropyl)-O'-[2-(3-mercaptopropionylamino)ethyl]polyethylene glycol, O,O'-bis[2-(N-succinimidylsuccinylamino)ethyl]polyethylene glycol, O,O'-bis(2-azidoethyl)polyethylene glycol, poly(ethylene glycol) diacrylate, poly(ethylene glycol) diglycidyl ether, poly(ethylene glycol) di(p-nitrophenyl carbonate), poly(ethylene glycol) di(vinyl sulfone), poly(ethylene glycol) di(proprionaldehyde), poly(ethylene glycol) di(benzotriazolyl carbonate), and the like, and combinations thereof. In some embodiments, the PEGylating component is α-succinimidyloxy-glutaryl-ω-succinimidyloxyglutaryloxypolyoxyethylene (SG-PEG-SG). SG-PEG-SG is believed to crosslink proteins and peptides via elimination of N-hydroxysuccinimide by the protein/peptide amino groups, forming carbamate bridges between multiple protein segments and the PEGylating agents. Thus, it is believed that the PEGylating agent forms a bridge between protein and peptide moieties.

In some embodiments, the PEGylating component used as crosslinking agents are 2-Arm PEG: α-succinimidyloxyglutaryl-ω-succinimidyloxyglutaryloxypolyoxyethylene and 4-Arm PEG: pentaerythritol tetra(succinmidyloxyglutaryl) polyoxyethylene.

In some embodiments, the method to treat cartilage and pen-cartilage wherein a pseudoplastic scaffold is hydrated with a fluid. In some embodiments, the mobile phase of the fluid is water, isotonic saline, balanced salt solution, buffer solution, Ringer's solution, cell culture media, stem cell media, serum, plasma, amniotic fluid, Wharton's jelly, nutrient broth, antiseptic solutions, or a combination thereof. In some embodiments where the fluid is an aqueous media, the aqueous media can have a pH in the range 4.5 to 8.0, or 5.5 to 7.5. In some embodiments, the fluid is a biological fluid selected from, but not limited to, cell culture media, stem cell media, serum, plasma, amniotic fluid, Wharton's jelly, or nutrient broth.

In some embodiments, the method to treat cartilage and peri-cartilage wherein the pseudoplastic scaffold includes an antimicrobial agent to hinder development and proliferation of microorganisms. In some embodiments, the addition of an antimicrobial agent helps reduce or eliminate microbial colonies and biofilm formation. Because of the possibility of infection in voids, wounds, and burns, the PEGylated composition can include a biological agent in an amount sufficient to hinder or eradicate microorganisms. Examples of biological agents include, but are not limited to, antibiotics, antiseptics, anti-infective agents, antimicrobial agents, antibacterial agents, antifungal agents, antiviral agents, antiprotozoal agents, sporicidal agents, and antiparasitic agents. In some embodiments, the biological agent is biodegradable, non-cytotoxic to human and animal cells, or both biodegradable and non-cytotoxic.

In some embodiments, the method to treat cartilage and peri-cartilage wherein the pseudoplastic scaffold described herein includes a biocidal agent. In some embodiments, the biocidal agents can include, but are not limited to, biguanides, such as poly(hexamethylene biguanide) (PHMB) and its salts, a low molecular weight synthetic cationic biguanide polymer, chlorhexidine and its salts, such as chlorhexidine digluconate, and alexidine and its salts, such as alexidine dihydrochloride, where the latter two are bis(biguanides), benzalkonium chloride, benzethonium chloride, cetyltrimethylammonium bromide, glycerol mono-laurate, capryl glycol, gentamicin sulfate, iodine, povidone iodine, starch-iodine, neomycin sulfate, polymyxin B, bacitracin, tetracyclines, clindamycin, gentamicin, nitrofurazone, mafenide acetate, copper and its salts, silver nanoparticles, silver sulfadiazine, silver nitrate, terbinafine hydrochloride, miconazole nitrate, ketoconazole, clotrimazole, itraconazole, metronidazole, antimicrobial peptides, polyquaternium-1,polyquaternium-6, polyquaternium-10, salts thereof, and combinations thereof.

In some embodiments, the method to treat cartilage and peri-cartilage wherein the pseudoplastic scaffold described herein, where the antimicrobial biguanide is poly(hexamethylene biguanide) hydrochloride (PHMB). PHMB can be used because of its high biocidal activity against microorganisms, combined with its biodegradation and low cytotoxicity. PHMB is primarily active against Gram-negative and Gram-positive bacteria, fungi, and viruses. In contrast to antibiotics, which are considered regulated pharmaceutical drugs and to which bacterial resistance can occur, such resistance does not occur with PHMB. As used herein, an "antimicrobial agent" is a substance that kills microorganisms or inhibits their growth or replication, while an "anti-infective agent" is a substance that counteracts infection by killing infectious agents, such as microorganisms, or preventing them from spreading. Often, the two terms are used interchangeably. As used herein, "PHMB" is considered an antimicrobial agent.

In some embodiments, the method to treat cartilage and peri-cartilage wherein the pseudoplastic scaffold described herein can include biocidal PHMB at a concentration ranging from 0.0001 wt % (1 ppm) to 1 wt % (10,000 ppm), or ranging from 0.01 wt % (100 ppm) to 0.75 wt % (7,500 ppm), or ranging from 0.05 wt % (500 ppm) to 0.5 wt % (5,000 ppm), or ranging from 0.1 wt % (1,000 ppm) to 0.25 wt % (2,500 ppm), based on the total weight of the composition. In some embodiments, the method to treat cartilage and peri-cartilage wherein dry hydrolyzed collagen and microgel compositions described herein can include biocidal PHMB at a concentration ranging from 0.002 wt % (20 ppm) to 25.0 wt % (250,000 ppm), or ranging from 0.20 wt % (2,000 ppm) to 15.0 wt % (150,000 ppm), or ranging from 1.0 wt % (10,000 ppm) to 10.0 wt % (100,000 ppm), or ranging from 2.0 wt % (20,000 ppm) to 4.0 wt % (40,000 ppm), based on the total weight of the composition.

In some embodiments, bis(biguanide)s, such as alexidine and its salts and chlorhexidine and its salts, can be added to the antimicrobial pseudoplastic scaffold in concentrations from 0.001 wt % (10 ppm) to 4.0 wt % (40,000 ppm).

In some embodiments, the method to treat cartilage and peri-cartilage wherein the pseudoplastic scaffold described herein can include surfactant-type antimicrobial agents, such as benzethonium chloride or benzalkonium chloride, in concentrations from 0.001 wt % (10 ppm) to 2.0 wt % (20,000 ppm).

In some embodiments, the method to treat cartilage and peri-cartilage wherein the pseudoplastic scaffold described herein can include lipophilic-type antimicrobial agents, such as glycerol monolaurate or capryl glycol, in concentrations from 0.1 wt % (1,000 ppm) to 2.0 wt % (20,000 ppm).

In some embodiments, the method to treat cartilage and peri-cartilage wherein the pseudoplastic scaffold described herein can include antimicrobial agents with reactive functional groups, such as amino, imino, imidazoyl, sulfhydryl, hydroxyl, phenolic, indolyl, guanidium, guanidinium, and carboxyl groups. These antimicrobial agents with reactive functional groups can be covalently incorporated into the pseudoplastic scaffold comprised of PEGylated protein-containing microgel or hydrolyzed collagen.

In some embodiments, the method to treat cartilage and peri-cartilage wherein the pseudoplastic scaffold described herein can include an aqueous solution (e.g., carrier fluid) with amniotic fluid, morselized amniotic tissue, minced tissue, micronized tissue, micronized decellularized tissue, exosomes, plasma, blood, granulated cross-linked bovine tendon collagen and glycosaminoglycans, cells and stem cells in cell culture medium, decellularized extracellular matrix derived from stem cells, synthetic or naturally derived extracellular matrix components, including collagen, glycosaminoglycans, fibrin, laminin, and fibronectin, hydroxyapatite, honey, polysaccharides, biodegradable polymers, including polyglycolides, polylactides, poly(lactide-co-glycolide), polydioxanone, polycaprolactone, poly (trimethylene carbonate), poly(propylene fumarate), polyurethanes, poly(ester amide)s, poly(ortho ester)s, polyanhydrides, poly(amino acid)s, polyphosphazenes, and bacterial polyesters, and combinations thereof, and which can be injected into soft tissue, a void or a wound.

In some embodiments, minced tissue can be selected from cartilage tissue, muscle tissue, vascular tissue, nerve tissue, fat tissue, skin tissue, bone tissue, tendon tissue, bladder tissue, intestinal tissue, heart tissue, lung tissue, kidney tissue, liver tissue, pancreatic tissue, and vocal fold tissue. In some embodiments, micronized tissues and micronized decellularized tissues can be selected from cartilage tissue, muscle tissue, vascular tissue, nerve tissue, fat tissue, skin tissue, bone tissue, tendon tissue, bladder tissue, intestinal tissue, heart tissue, lung tissue, kidney tissue, liver tissue, pancreatic tissue, and vocal fold tissue.

The method to treat cartilage and peri-cartilage wherein the pseudoplastic scaffold described herein can be used, for example, for the treatment of impaired tissue due to inflammation, trauma, disease or where increased cellular metabolic activity is desired.

In some embodiments, when the method to treat cartilage and peri-cartilage wherein the pseudoplastic scaffold described herein is used as a cell scaffold, the pseudoplastic scaffold can be in the form of a powder and can be rapidly rehydrated by a solution containing cells. In some embodiments, the method to treat cartilage and peri-cartilage wherein a powder of the pseudoplastic scaffold is preloaded in a syringe, and cells are drawn into the syringe in order to hydrate the powder before the cell-laden composition is injected into a wound or defect. In other embodiments, the pseudoplastic scaffold powder is preloaded in a vial, then cells in solution are injected through the septum into the vial in order to hydrate the powder, before the cell-laden system is drawn into a syringe and injected into tissue, a void, or a wound in need thereof. In some embodiments, the hydrated pseudoplastic scaffold comprising cells can be injected through a syringe or cannula into tissue, a void, or a wound or applied by coating for localized delivery. Upon application (removal of shear), the hydrated flowable pseudoplastic scaffold forms a stationary hydrogel which adheres to the surrounding tissue. The shear thinning and rapid hydrogel formation characteristics of the pseudoplastic scaffold, in conjunction with its ability to accommodate cells and other biological agents in void spaces, coupled with its ability to fill the shape of the cavity with an interface between the hydrogel and tissue, provides a superior composition for delivery of biological agents. As a result, the pseudoplastic scaffold described herein provides an excellent system for cell delivery.

In some embodiments where the method to treat cartilage and pen-cartilage wherein the pseudoplastic scaffold described herein is an aqueous-based solution, gel, paste, emulsion, or foam, a water-soluble polymer can be added to increase solution viscosity and to prolong residence time on the surface of cartilage and pen-cartilage, void, or wound, or subcutaneously in a cartilage or pen-cartilage void or wound. In some embodiments, useful water-soluble polymers include, but are not limited to, poly(ethylene glycol), poly(ethylene oxide), poly(vinyl alcohol) and copolymers, poly(N-vinylpyrrolidone) and copolymers, methylcellulose, hydroxyethylcellulose, hydroxypropylcellulose, hydroxypropylmethylcellulose, carboxymethylcellulose, guar gum, hydroxyethylguar, hydroxypropylguar, gelatin, albumin, maltodextrin, hydroxypropylmethylguar, carboxymethylguar, carboxymethylchitosan, locust bean gum, carrageenan, xanthan gum, gellan gum, pullulan, alginate, chondroitin sulfate, dextran, dextran sulfate, Aloe vera gel, scleroglucan, schizophyllan, gum arabic, tamarind gum, poly(methyl vinyl ether), ethylene oxide-propylene oxide-ethylene oxide block copolymers, hyaluronan, chondroitin sulfate, keratan sulfate, dermatan sulfate, heparan sulfate, dextran, carbomer and its salts, poly(acrylic acid) and its salts, poly(methacrylic acid) and its salts, poly(ethylene-co-acrylic acid), poly(vinyl methyl ether), poly(vinylphosphoric acid) salts, poly(vinylsulfonic acid) salts, sodium poly(2-acrylamido-2-methylpropanesulfonate), polyacrylamide(s), poly(N,N-dimethylacrylamide), poly(N-vinylacetamide), poly(N-vinylformamide), poly(2-hydroxyethyl methacrylate), poly (glyceryl methacrylate), poly(2-ethyl-2-oxazoline), poly(N-isopropylacrylamide) and poly(N-vinylcaprolactam), the latter two hydrated below their Lower Critical Solution Temperatures, polyquaternium-1, polyquaternium-6, polyquaternium-10, ionene polymers, cationic guar, pyridinium polymers, imidazolium polymers, diallyldimethylammonium polymers, acryloyl-, methacryloyl-, and styryl-trimethylammonium polymers, acrylamido- and methacrylamido-trimethylammonium polymers, and the like, and derivatives and combinations thereof.

In some embodiments, the pseudoplastic scaffold compositions in the form of viscous solutions, gels, creams, pastes, emulsion, balms, and sprays, can be facilitated by the inclusion of water-soluble polymer viscosity builders in amounts ranging from about 0.01 to about 50.0 wt %, from 0.1 to 45 wt %, or from 1.0 to 10.0 wt %.

In some embodiments, the composition is applied topically, via injection, or via ingestion.

As used herein, "topically" has its standard meaning (e.g., directly onto tissue) and includes applying onto a surface of cartilage (e.g., during a surgical intervention).

When injected, the injection can be intradermal, subcutaneous, oral, intramuscular, submucosal, intranasal, vaginal, buccal, intrathecal, epidural, intraparenchymal, ocular, subretinal, dental, intra-tumoral, intracardiac, intra-articular, intravenous, intracavernous, intraosseous, intraperitoneal, intra-abdominal, intra-fascial, intra-organ, and intravitreal.

In some embodiments, the contacting step comprises topical application of the pseudoplastic scaffold. In some embodiments, the pseudoplastic scaffold is applied as a powder.

In some embodiments, the contacting step comprises topical application of the pseudoplastic scaffold. In some embodiments, the pseudoplastic scaffold is applied as a hydrated powder.

In some embodiments, the contacting step comprises injection into cartilage or peri-cartilage.

In some embodiments, the contacting step occurs during a surgical procedure. In some embodiments, the pseudoplastic scaffold is applied topically to fill surrounding voids.

In some embodiments, the method to treat cartilage and pen-cartilage wherein the pseudoplastic scaffold described herein may contain chlorophyllin, a water-soluble semi-synthetic derivative of chlorophyll which may be used to provide anti-inflammatory properties. In some embodiments, chlorophyllin can be present in an amount ranging from 0% to 5 wt % based on the weight of the pseudoplastic scaffold. In some embodiments, chlorophyllin can be present in an amount of at least 0.1 wt %, or at least 0.25 wt %, or at least 0.5 wt % based on the weight of the pseudoplastic scaffold.

In some embodiments, the method to treat cartilage and peri-cartilage wherein the pseudoplastic scaffold described herein can also include wetting agents, buffers, gelling agents or emulsifiers. Other excipients could include various water-based buffers ranging in pH from 5.0-7.5, surfactants, silicones, polyether copolymers, vegetable and plant fats and oils, hydrophilic and hydrophobic alcohols, vitamins, monoglycerides, laurate esters, myristate esters, palmitate esters, and stearate esters. In some embodiments, the method to treat cartilage and peri-cartilage wherein the pseudoplastic scaffold can be in a form including, but not limited to, liquid, gel, paste, cream, emulsion, combinations thereof, and the like.

In some embodiments, the method to treat cartilage and peri-cartilage wherein the pseudoplastic scaffold described herein is a dry powder. The pseudoplastic scaffold may be used in powder form, or the powder may be further processed (e.g., rehydrated) into solutions, suspensions, creams, lotions, gels, pastes, emulsions, balms, sprays, foams, aerosols, films, or other formulations before application to injured or compromised tissue.

As used herein, "aqueous media" refers to a spectrum of water-based solutions including, but not limited to, homogeneous solutions in water with solubilized components, cell media solutions, buffer solutions, isotonic solutions, salt solutions, emulsified solutions, surfactant solutions, amniotic fluids, Wharton's jelly, serum, blood, plasma, hydrophilic polymers, and viscous or gelled homogeneous or emulsified solutions in water.

As used herein, "surfactant" has its standard meaning and includes compounds that lower the surface tension (or interfacial tension) between two liquids or between a liquid and a solid and includes emulsifying agents, emulsifiers, detergents, wetting agents, and surface-active agents.

As used herein, "hydrophilic" has its standard meaning and includes compounds and materials that have an affinity to water and can be ionic or neutral or have polar groups in their structure that attract water. For example, hydrophilic compounds can be miscible, swellable, adsorbable, or soluble in water, with a stationary contact angle with water of ≤900 in water at room temperature.

As used herein, "hydrophobic" refers to repelling water, being insoluble or relatively insoluble in water, and lacking an affinity for water with a stationary contact angle with water of ≥90° in water at room temperature. Hydrophobic compounds with hydrophilic substituents, such as vicinal dials, may form emulsions in water, with or without added surfactant, with the hydrophilic substituent at the water interface and the hydrophobic portion of the compound in the interior of the emulsion.

As used herein, "swellable" refers to materials that uptake, absorb and/or adsorb fluids to their functional groups, surfaces, pores, micropores, nanopores, holes, and interstitial networks.

As used herein, the term "PEGylation" pertains to modifying hydrolyzed collagen or a protein or protein-based macromolecule by covalently attaching poly(ethylene glycol) (PEG) with reactive substituents to the available reactive functional groups on protein or hydrolyzed collagen, such as amino groups or sulfhydryl groups, whereas "PEGylated" refers to a protein or hydrolyzed collagen having a PEG substituent attached thereto.

As used herein, "proteins" is intended to include protein-based macromolecules and includes extracellular matrices, glycoproteins, structural proteins, fibrous proteins, enzymes, proteoglycans, natural polypeptides, synthetic polypeptides, globular proteins, membrane proteins, plasma proteins, peptides, antimicrobial peptides, peptide hormones, chaperones, metalloproteins, hemoproteins, coagulation proteins, immune system proteins, ion channel proteins, cell adhesion proteins, neuropeptides, nucleoproteins, scleroproteins, chromoproteins, conjugated proteins, protein-protein complexes, protein-polysaccharide complexes, protein-lipid complexes, protein-enzyme complexes, protein-polymer complexes, motor proteins, mucoproteins, phosphoproteins, contractile proteins, transport proteins, signaling proteins, regulatory proteins, growth factors proteins, sensory proteins, defense proteins, storage proteins, receptor proteins, antibodies, recombinant proteins, fibrinogen, fibrin, thrombin, collagen, elastin, albumin, gelatin, keratin, laminin, and combinations thereof. Hydrolyzed collagens are sufficiently degraded that they are not considered proteins.

As used herein, "peptides" are short chains of two or more amino acids linked by peptide bonds. Peptides that have a molar mass of 12,000 Da or higher are "proteins". Peptides include hydrolyzed collagen, aeruginosins, cyanopeptolins, microcystins, microviridins, microginins, anabaenopeptins, cyclamides, teprotide, glutathione, and combinations thereof.

As used herein, "derivatized proteins" are protein components attached, bound, coordinated, or complexed with another material, such as other proteins, polysaccharides, oligosaccharides, glycosaminoglycans, lipids, phospholipids, liposomes, synthetic polypeptides, DNA, RNA, synthetic polymers, surfactants, metal atoms, nanoparticles, antimicrobial agents, antibiotics, drugs, salts thereof, and the like.

As used herein, a "hydrogel" is an insoluble polymeric network composed of macromolecules that are normally water-soluble but that are insoluble because they are cross-linked or pseudo-crosslinked by covalent, ionic, or physical interaction among macromolecular chains, where the insoluble network adsorbs at least 10% of its weight in water. A hydrogel may contain one or more hydrophilic polymeric species.

As used herein, a "microgel" is a gelatinous, water insoluble, hydrophilic particle ranging in length from 1 micrometer to 1,000 micrometers, with diameters of 1 micrometer to 1,000 micrometers or a dehydrated particle capable of exhibiting those properties when hydrated.

As used herein, "microgel particles" are mixed particles of water-insoluble, water-swellable gel fragments that have varied shapes, including spherical, elliptical, angular, regular (organized) or irregular shapes, either hollow, microporous, mesoporous, macroporous, or with void spaces, or a combination thereof, depending on the method of formation.

As used herein, "hydrolyzed collagen and microgel compositions" and "PEGylated compounds" and "pseudoplastic scaffolds", are used to refer to compositions containing both hydrolyzed collagen and PEGylated protein-containing microgels, such as PEGylated microgel networks and PEGylated protein-hydrolyzed collagen (PHC)-containing microgels as used herein.

As used herein, "flowable" pertains to a volume of fluid or gel that is capable of flowing through a passageway of any given dimension, such as through a squeeze tube, pump, cannula, or syringe.

As used herein, "injectable" describes the ability of a solution, suspension, gel, emulsion, or microgel to pass through a hypodermic needle or cannula.

As used herein, "pseudoplastic" pertains to a fluid composition having a viscosity that decreases with increasing shear rate, that is, shear thinning.

As used herein, "biologically active agents" has its standard meaning and includes chemical or biological substances or formulations that beneficially affect human or animal health and well-being or is intended for use in the cure, mitigation, treatment, prevention, or diagnosis of infection or disease, or is destructive to or inhibits the growth of microorganisms.

As used herein, "antimicrobial agent" has its standard meaning and includes a substance that kills microorganisms or inhibits their growth or replication, while an "anti-infective agent" is defined as a substance that counteracts infection by killing infectious agents, such as microorganisms, or preventing them from spreading. Often, the two terms are used interchangeably.

As used herein, "antibiotic" has its standard meaning and includes those substances that were originally produced by a microorganism or synthesized with active properties that can kill or prevent the growth of another microorganism. The term antibiotic is commonly used to refer to almost any prescribed drug that attempts to eliminate infection.

As used herein, "excipient" has its standard meaning and includes inert substances that form a vehicle, such as a liquid, fluid, or gel, that solubilizes or disperses a hydrolyzed collagen and microgel composition, which may include other added ingredients.

As used herein, "peri-cartilage" has its standard meaning and includes biological matter integrally connected to cartilage, for example, subchondral bone and perichondrium.

In some embodiments, the method to treat cartilage and peri-cartilage wherein the pseudoplastic scaffold described herein where one or more observational or detectable agents may be incorporated into the pseudoplastic scaffold to provide enhanced visualization or facilitate proper placement. The agents may comprise, in other embodiments, dyes, fluorescent substances, ultraviolet absorbers, radioactive substances, pigments, or any combinations thereof.

In some embodiments, the method to treat cartilage and peri-cartilage wherein one or more biologically active agents may be incorporated into the pseudoplastic scaffold to provide a medical benefit to a mammalian host. Examples of biologically active agents that can be incorporated into the pseudoplastic scaffold include, but are not limited to, cells, stem cells, amniotic tissue, amiotic cells, exosomes, growth factors, decellularized extracellular matrix derived from stem cells, micronized decellularized tissue, granulated crosslinked bovine tendon collagen and glycosaminoglycans, antibiotics, antiseptics, anti-infective agents, antimicrobial agents, antibacterial agents, antifungal agents, antiviral agents, antiprotozoal agents, sporicidal agents, antiparasitic agents, peripheral neuropathy agents, neuropathic agents, chemotactic agents, analgesic agents, anti-inflammatory agents, anti-allergic agents, anti-hypertension agents, mitomycin-type antibiotics, polyene antifungal agents, antiperspirant agents, decongestants, anti-kinetosis agents, central nervous system agents, wound healing agents, anti-VEGF agents, anti-tumor agents, escharotic agents, anti-psoriasis agents, anti-diabetic agents, anti-arthritis agents, anti-itching agents, antipruritic agents, anesthetic agents, anti-malarial agents, dermatological agents, anti-arrhythmic agents, anti-convulsants, antiemetic agents, anti-rheumatoid agents, anti-androgenic agents, anthracyclines, anti-acne agents, anticholinergic agents, anti-aging agents, antihistamines, anti-parasitic agents, hemostatic agents, vasoconstrictors, vasodilators, thrombogenic agents, anti-clotting agents, cardiovascular agents, angina agents, erectile dysfunction agents, sex hormones, growth hormones, isoflavones, integrin binding sequences, biologically active ligands, cell attachment mediators, immunomodulators, tumor necrosis factor alpha, anti-cancer agents, anti-depressant agents, antitussive agents, anti-neoplastic agents, narcotic antagonists, anti-hypercholesterolemia agents, apoptosis-inducing agents, emollients, alpha-hydroxyl acids, manuka honey, retinoids, hormones, tumor-specific antibodies, antisense oligonucleotides, small interfering RNA (siRNA), anti-VEGF RNA aptamer, nucleic acids, DNA, DNA fragments, DNA plasmids, Si-RNA, transfection agents, vitamins, essential oils, liposomes, silver nanoparticles, gold nanoparticles, drug-containing nanoparticles, albumin-based nanoparticles, chitosan-containing nanoparticles, polysaccharide-based nanoparticles, dendrimer nanoparticles, phospholipid nanoparticles, iron oxide nanoparticles, bismuth nanoparticles, gadolinium nanoparticles, metallic nanoparticles, ceramic nanoparticles, silica-based nanoparticles, virus-based nanoparticles, virus-like nanoparticles, antibiotic-containing nanoparticles, nitric oxide-containing nanoparticles, nanoshells, nanorods, polymeric micelles, silver salts, zinc salts, quantum dots nanoparticles, polymer-based microparticles, polymer-based microspheres, drug-containing microparticles, drug-containing microspheres, antibiotic-containing microparticles, antibiotic-containing microspheres, antimicrobial microparticles, antimicrobial microspheres, salicylic acid, benzoyl peroxide, 5-fluorouracil, nicotinic acid, nitroglycerin, clonidine, estradiol, testosterone, nicotine, scopolamine, fentanyl, diclofenac, buprenorphine, bupivacaine, ketoprofen, opioids, cannabinoids, enzymes, enzyme inhibitors, oligopeptides, cyclopeptides, polypeptides, proteins, prodrugs, protease inhibitors, cytokines, hyaluronic acid, chondroitin sulfate, dermatan sulfate, para-sympatholytic agents, chelating agents, hair growth agents, lipids, glycolipids, glycoproteins, endocrine hormones, growth hormones, growth factors, differentiation factors, heat shock proteins, immunological response modifiers, saccharides, polysaccharides, insulin and insulin derivatives, steroids, corticosteroids, and non-steroidal anti-inflammatory drugs or similar materials, in either their salt form or their neutral form, either being inherently hydrophilic or encapsulated within a hydrophilic microparticle or nanoparticle. Such biologically active agents could be in either of the (R)-, (R, S)-, or (S)-configuration, or a combination thereof.

As used herein, "cell culture" has its standard meaning and includes the transfer of cells, tissues or organs from an animal or plant and their subsequent placement into an environment conducive to or for evaluating their survival and/or proliferation.

As used herein, "MTT Assay" has its standard meaning and is a test for cell metabolic activity related to cell viability and proliferation or cytotoxicity.

In some embodiments, the method to treat cartilage and peri-cartilage wherein the pseudoplastic scaffold described herein may include cells. Examples of cells useful in the pseudoplastic scaffold described herein include, but are not limited to, chondrocytes, chondrons, osteoblasts, fibroblasts, keratinocytes, neurons, glial cells, astrocytes, Schwarm cells, dorsal root ganglia, adipocytes, endothelial cells, epithelial cells, fibrochondrocytes, myocytes, cardiomyocytes, myoblasts, hepatocytes, tenocytes, intestinal epithelial cells, smooth muscle cells, stromal cells, neutrophils, lymphocytes, bone marrow cells, platelets, and combinations thereof. In some embodiments, the cells are eukaryotic or mammalian. In some embodiments, the cells are of human origin. In some embodiments, the cells may be autologous or allogeneic.

In some embodiments the method to treat cartilage and pen-cartilage wherein the pseudoplastic scaffold described herein may include adult stem cells, embryonic stem cells, amniotic stem cells, induced pluripotent stem cells, fetal stem cells, tissue stem cells, adipose-derived stem cells, bone marrow stem cells, human umbilical cord blood stem cells, blood progenitor cells, mesenchymal stem cells, hematopoietic stem cells, epidermal stem cells, endothelial progenitor cells, epithelial stem cells, epiblast stem cells, cardiac stem cells, pancreatic stem cells, neural stem cells, limbal stem cells, perinatal stem cells, satellite cells, side population cells, multipotent stem cells, totipotent stem cells, unipotent stem cells, and combinations thereof. In some embodiments, the stem cells are mammalian. In some embodiments, the stem cells are of human origin. In some embodiments, the stem cells may be autologous or allogeneic.

In some embodiments, the method to treat cartilage and peri-cartilage wherein the pseudoplastic scaffold described herein may be used as a scaffold matrix to deliver a therapeutically effective amount of between 10,000 cells to about 1 billion or more cells. In some embodiments, products derived from placental tissue may be incorporated with the pseudoplastic scaffold for placement into a mammalian host. Placental tissues are a source of collagen, elastin, fibronectin, and growth factors, including platelet-derived growth factor (PDGF), vascular endothelial growth factor (VEGF), epidermal growth factor (EGF), fibroblast growth factor (FGF), and transforming growth factor beta (TGF-β), which can support tissue repair and regeneration. In particular, amniotic tissue has anti-adhesive and antimicrobial properties, and such tissue has been shown to support cartilage and peri-cartilage repair, reduce inflammation and minimize scar tissue formation, which are significant benefits in the treatment of cartilage and peri-cartilage injuries.

Amniotic tissues have been described as immune privileged in that an immune response in the human body rarely occurs in response to the introduction of amniotic tissue. In some embodiments a morselized, flowable tissue allograft derived from amniotic tissues can be added to the pseudoplastic scaffold for a coating or injection into soft tissue, or placement surrounding a tissue replacement product.

In some embodiments, the method to treat cartilage and peri-cartilage wherein the pseudoplastic scaffold described herein may include growth factors. Examples of useful growth factors include, but are not limited to, epidermal growth factor (EGF), transforming growth factor beta (TGF-β), fibroblast growth factor (FGF), vascular endothelial growth factor (VEGF), granulocyte macrophage colony stimulating factor (GM-CSF), platelet-derived growth factor (PDGF), connective tissue growth factor (CTGF), insulin-like growth factor (IGF), keratinocyte growth factor (KGF), interleukin (IL) family, stromal cell derived factor (SDF), heparin binding growth factor (HBGF), nerve growth factor (NGF), brain-derived neurotrophic factor (BDNF), growth differentiation factor (GDF), muscle morphogenic factor (MMF), tumor necrosis factor-alpha (TNFα), and bone morphogenetic proteins (BMP).

In some embodiments, the method to treat cartilage and pen-cartilage wherein the pseudoplastic scaffold described herein can be used as an injectable biological tissue void filler and may also include any other component suitable for augmenting, strengthening, supporting, repairing, rebuilding, healing, occluding or filling biological tissue.

In some embodiments, the method to treat cartilage and pen-cartilage wherein the pseudoplastic scaffold described herein can be in a form selected from, but not limited to, a powder, a film, a foam, a dressing, a roll, a fiber or fibrous material, or a coating. In some embodiments, the resulting pseudoplastic scaffold is insoluble, but swellable.

In some embodiments, the method to treat cartilage and peri-cartilage wherein the pseudoplastic scaffold described herein can absorb at least 2 times its dry weight of saline, or at least 5 times, or at least 10 times, or at least 20 times, or at least 30 times, or at least 40 times, or at least 50 times its dry weight of saline.

In another aspect, the method to treat cartilage and peri-cartilage wherein the pseudoplastic scaffold described herein contacts impaired cartilage and peri-cartilage.

In some embodiments, the method to treat cartilage and peri-cartilage wherein the pseudoplastic scaffold described herein further comprises biologic components such as cells, minced tissue, extracellular matrix, reactive proteins, polysaccharides, and biologic fluids.

In some embodiments, the method to treat cartilage and peri-cartilage wherein the contacting step comprises applying the pseudoplastic scaffold within tissue. In some embodiments, the pseudoplastic scaffold is applied subcutaneously. In some embodiments, the pseudoplastic scaffold is applied via injection. In some embodiments, the pseudoplastic scaffold is applied using a syringe (without a needle) or tube.

In some methods of cartilage and peri-cartilage treatment embodiments, the contacting step comprises topical application of the pseudoplastic scaffold.

In some methods of cartilage and peri-cartilage treatment embodiments, the pseudoplastic scaffold comprises a PEGylated microgel network formed by combining the PEGylated protein-containing microgel and the hydrolyzed collagen component in a liquid carrier.

In some methods of cartilage and peri-cartilage treatment embodiments, the pseudoplastic scaffold comprises a PEGylated PHC-containing microgel formed when the hydrolyzed collagen component is present when the protein component is crosslinked by the PEGylating component. In some embodiments, the hydrolyzed collagen component is crosslinked with the PEGylating component.

In some methods of cartilage and pen-cartilage treatment embodiments, the impaired tissue is at least one of inflamed tissue, diseased tissue, a cut, a wound, a lesion, a fistula, a burn, a void, a surgical site, a blunt injury site, a biopsy site, a surgical site, or a medical implant site.

Any of the compositions described herein can be used for treatment of cartilage and peri-cartilage. In some examples, the compositions can be used for injection into biological tissue. The injection can be intradermal, subcutaneous, oral, intramuscular, submucosal, intranasal, vaginal, buccal, intrathecal, epidural, intraparenchymal, ocular, subretinal, dental, intra-tumoral, intracardiac, intra-articular, intravenous, intra-cavernous, intraosseous, intraperitoneal, intra-abdominal, intra-fascial, intra-organ, and intravitreal. In some embodiments, the pseudoplastic scaffolds described herein are in the form of a dry powder, and the use and or method further comprises hydrating the dry powder prior to the injection step.

EXPERIMENTAL

The following materials and abbreviations are used in the experimental section.

| Material | Manufacturer | Lot |
|---|---|---|
| Blunt Fill Needle 18G | BD | 4122756 |
| Saline: Sodium chloride solution 0.90 (w/v) in water | VWR | 19C2056744 |
| Porcine Medella Pro 100 | Gelita | 1010583 |
| Porkskin Gelatin 275 B L | Gelita | 614276 |
| Porkskin Gelatin 200 BL | Gelita | 614538 |
| Limed Bone Gelatin Bovine 150 BL | Gelita | 613582, 614901 |
| Limed Bone Gelatin Bovine 200 BL | Gelita | 614679 |
| Hydrolyzed Collagen-bovine | Gelita Peptiplus XB | 8622174, 8621390-082322 |
| Hydrolyzed collagen-bovine, chicken. Marine, eggshell | Wholesome Wellness Hydrolyzed Multi Collagen | AZ13124 |
| Hydrolyzed collagen-marine | Anthony's Marine Hydrolyzed Collagen | F242434 |
| Pullulan 90-130 mm^2/s | BOC | B21B07131 |
| Micronized SIS | Wound Care Innovations Fortify TRG | LB13114427 |
| Bioglass | Schott MD01 | 1137402 |
| PLA: Poly(lactic acid) | Gelatex | B230233 |
| Lidocaine | Tropicaine Products | NA |
| Aspirin | Spectrum | 2GC0115 |
| Vitamin C | Spectrum | 1HF0586 |
| PHMB: Poly(hexamethylene biguanide) | Lonza Cosmocil CQ | 14GR100230 |
| 2-Arm PEG B: α-succinimidyloxyglutaryl-ω-succinimidyloxyglutaryloxypolyoxyethylene | Broadpharma PEG-bis-succinimidyl-oxyglutaryl (MW 1000) | 20230811A |
| 2-Arm PEG N: α-succinimidyloxyglutaryl-ω-succinimidyloxyglutaryloxypolyoxyethylene | NOF:Sunbright DE-034GS (MW 3,400) | M83541, M153605 |
| 4-Arm PEG: pentaerythritol tetra(succinmidyloxyglutaryl)polyoxyethylene | NOF: Sunbright PTE-050GS (MW 5,000) | M196635 |
| Viable bovine cartilage explants | Articular Engineering | |
| LDH Cytotoxicity Detection Kit | Roche | 11644793001 |
| Sulfated Glycosaminoglycan Assay Kit | Blyscan | B1000 |

Example 1. Hydrolyzed Collagen Mixtures with Microgel

PEGylated protein-containing microgels were prepared at a mole ratio of 10 parts PEG to 1 part gelatin. Porcine gelatin (200 bloom) was dissolved in deionized (DI) water at 70° C. (Part B). 2-arm PEG B (MW 1,000) was dissolved in DI water at room temperature (~22° C.) (PartA). The PEG solution (Part A) was blended with the gelatin solution (Part B) and reacted overnight at room temperature, then frozen at −80 mC. The resulting mixture was lyophilized and then ground to form white microgel powder. Hydrolyzed collagen-bovine powder (Part C) was then blended into the microgel powder to produce a blended HC/microgel powder (Table 1). As shown in Table 1, Formula A included 1 part bovine hydrolyzed collagen, while Formula B included 10 parts bovine hydrolyzed collagen.

Figure 1:
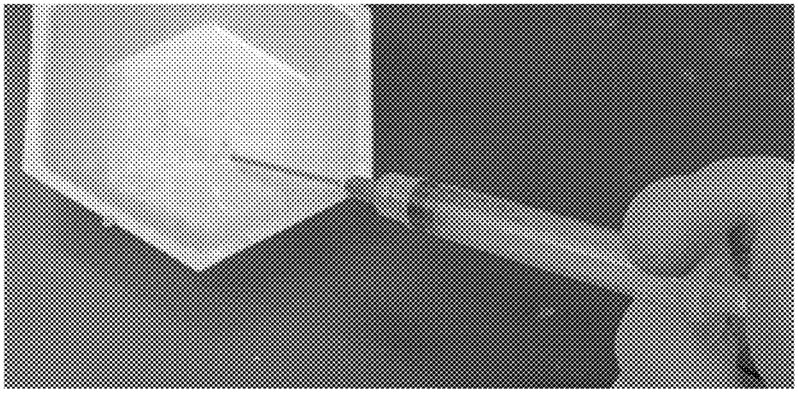
FIG. 1 shows an aqueous scaffold of PEGylated microgel with hydrolyzed collagen that exhibits pseudoplastic hydrogel properties that allow it to be drawn into a syringe.

The powder mixtures were hydrated with saline for less than a minute and found to be pseudoplastic hydrogels that could be dispensed through a cannula (e.g., FIG. 1). Formula A absorbed up to 18 times its weight in saline while retaining its pseudoplastic gel properties. Formula B absorbed up to 8 times its weight in saline with retention of pseudoplastic hydrogel properties.

TABLE 1

| | Molar Ratio | | | Part A | | Part B | | Part C |
|---|---|---|---|---|---|---|---|---|
| Formula | 2-arm PEG | Gelatin | HC-bovine | 2-Arm Peg B (g) | Water (g) | Gelatin (g) | Water (g) | HC-bovine (g) |
| A | 10 | 1 | 1 | 0.225 | 10.038 | 1.001 | 10.006 | 0.067 |
| B | 10 | 1 | 10 | 0.112 | 10.010 | 0.501 | 10.005 | 0.334 |

Example 2: Hydrolyzed Collagen Mixture with Microgel

A PEGylated protein-containing microgel was prepared at a 10:1 mole ratio of PEG to gelatin. Porcine gelatin (275 bloom) was dissolved in deionized (DI) water at 70° C. (Part B), then 2-arm PEG N (3,400 Da) and 4-arm PEG were dissolved in DI water at room temperature (Part A). The PEG solution (Part A) was blended with the gelatin solution (Part B) and reacted overnight at room temperature, then frozen at −80° C. The resulting mixture was lyophilized and then ground to form white microgel powder (Table 2). A hydrolyzed collagen-bovine powder (1.2 g) was then blended with the PEGylated protein-containing microgel to produce a pseudoplastic scaffold.

The pseudoplastic scaffold (1.25 g) was hydrated with 1.2 g saline for 5 minutes at room temperature and was found to produce a flowable gel which could be dispensed through a cannula (e.g., FIG. 1).

TABLE 2

| | Molar Ratio | | | | Part A | | | Part B | |
|---|---|---|---|---|---|---|---|---|---|
| Formula | 2-Arm PEG | 4-Arm PEG | Gelatin | HC-Bovine | 2-Arm Peg N (g) | 4-Arm PEG (g) | Water (g) | Gelatin (g) | Water (g) |
| C | 9 | 1 | 1 | 63 | 0.222 | 0.037 | 10.016 | 0.501 | 10.010 |

Example 3: Hydrolyzed Collagen Mixture with Microgel and Antimicrobial

Bovine gelatin (150 bloom) and PHMB were dissolved in DI water at 70° C. (Part B). 2-arm PEG N (3,500 Mw) and 4-arm PEG were dissolved in DI water at room temperature (Part A). Parts A and B were blended at room temperature overnight and then frozen at −80° C. The resulting PEGylated protein-containing microgel mixture was lyophilized and then ground to form white microgel powder (Table 3).

TABLE 3

| | Molar Ratio | | | Part A | | | Part B | | |
|---|---|---|---|---|---|---|---|---|---|
| Formula | 2-Arm PEG | 4-Arm PEG | Gelatin | 2-Arm Peg (g) | 4-Arm Peg (g) | Water (g) | Gelatin (g) | Water (g) | PHMB (g) |
| D | 9 | 1 | 1 | 0.433 | 0.059 | 10.005 | 0.503 | 10.029 | 0.005 |

Hydrolyzed collagen-bovine powder (0.0067 g) was then blended into the PEGylated protein-containing microgel (0.105 g) to produce a pseudoplastic scaffold. The PEGylated composition (0.1115 g) was hydrated with 1.80 g saline for 5 minutes at room temperature and was found to produce a flowable hydrogel which could be dispensed through a cannula (FIG. 1). Upon removal of shear (vortexing) the gel was stationary.

Example 4: MTT Assay for Fibroblast Viability and Proliferation

PEGylated compositions were prepared as in Example 1 for Formulas G and H, which were PEGylated microgel networks. Formulas E and F differ as the hydrolyzed collagen-bovine was blended into the gelatin and was present during PEGylation (Table 4) to form a PEGylated PHC-containing microgel. Both formulas with 1 molar ratio of hydrolyzed collagen (E, G) absorbed 18 times their weight in saline and were pseudoplastic gels. Both formulas with 10 molar ratios of hydrolyzed collagen (F, H) absorbed 8 times their weight in saline and were pseudoplastic gels. Unexpectedly, whether the pseudoplastic scaffold was a PEGylated PHC-containing microgel or a PEGylated microgel network did not make a visible difference in the gel properties or saline absorption properties of the resulting rehydrated powder.

TABLE 4

| | Molar Ratio | | | Part A | | Part B | | Part C |
|---|---|---|---|---|---|---|---|---|
| Formula | PEG | Gelatin | HC-bovine | 2-Arm Peg (g) | Water (g) | Gelatin (g) | Water (g) | HC-bovine (g) |
| E | 10 | 1 | 1 | 0.223 | 10.032 | 1.001 | 10.009 | 0.067 |
| F | 10 | 1 | 10 | 0.112 | 10.028 | 0.501 | 10.011 | 0.334 |
| G | 10 | 1 | 1 | 0.225 | 10.038 | 1.001 | 10.006 | 0.067 |
| H | 10 | 1 | 10 | 0.112 | 10.010 | 0.501 | 10.005 | 0.334 |
| I | | | | | | 0.201 | | |
| J | | | | | | | | 2.801 |

These formulas (E to H in triplicate) were compared to an aqueous gelatin control (formula I) and aqueous hydrolyzed collagen control (formula J) using an MTT assay method to evaluate fibroblast attachment to the hydrated HC microgel formulations. Powder formulas E to J were hydrated with saline as shown in Table 5.

TABLE 5

| MTT Concentrations | | |
|---|---|---|
| Formula | Powder (g) | Saline (g) |
| E | 0.101 | 1.816 |
| F | 0.201 | 1.801 |
| G | 0.1 | 1.814 |
| H | 0.201 | 1.819 |
| I | 0.201 | 3.809 |
| J | 2.801 | 1.204 |

Primary human dermal fibroblasts (HDFa, PCS-201-012, P4) were grown to 100% confluency in a T75 flask with fibroblast basal medium. The cells were then detached, spun down, and resuspended in 2% low serum media containing penicillin/streptomycin/amphotericin B for infection prevention. The 24-well plates were treated with STEMCELL anti-adherence solution for 5 minutes and then rinsed twice with phosphate-buffered saline without calcium and magnesium. Millicell cell culture inserts (0.4 μm, 12 mm diameter) were added to each well, and 0.2 grams of sample were added to each insert. Subsequently, 50 μL of the cell suspension was added to each sample and incubated for 30 minutes, followed by the addition of 1 mL of low serum media with penicillin/streptomycin/amphotericin B. The plates were then placed back in the incubator for 24 hours. The next day, MTT (3-(4,5-dimethylthiazol-2-yl)-2,5-diphenyltetrazolium bromide) solution was used, and 1 mL of this solution was added to each well. The plate was incubated for 4 hours at 37° C. After incubation, the medium was removed from each well, and 1 mL of dimethyl sulfoxide (DMSO) was added to each well. Next, 200 μL from each well of the 24-well plate was transferred to a corresponding well in a 96-well plate. The plate reader then measured the absorbance of each well at 540 nm. The data were normalized using the 2% fibroblast basal media as the 100 percent (control). The results are shown in FIG. 3 which shows MTT data for hydrolyzed collagen with microgel compositions The MTT assay results shown in FIG. 3 indicate that both hydrolyzed collagen (101% CTRL) and gelatin (127% CTRL) provide improved viability compared to the control. Despite different formulating techniques, both the PEGylated PCH-containing microgel (Formula E) and the PEGylated microgel network (Formula G) containing 1:1 mole ratio of hydrolyzed collagen to gelatin demonstrate essentially identical viability results (130%) compared to the control. Also, despite different formulating technique, both the PEGylated PCH-containing microgel (Formula F) and the PEGylated microgel network (Formula H) containing a 10:1 mole ratio of hydrolyzed collagen to gelatin provide a similar improvement (182%, 175% CTRL) in fibroblast viability and proliferation. This data demonstrates the synergistic improvement in fibroblast viability and proliferation for pseudoplastic scaffolds described herein, which include both a PEGylated protein-containing microgel and hydrolyzed collagen.

Example 5: Hydrolyzed Collagen Source Comparisons—Marine, Bovine, Mixed

Lyophilized and powdered PEGylated protein-containing microgel (Formulation D) from Example 3 was blended with hydrolyzed collagen from bovine source (Peptiplus XB), from marine source (Anthony's Marine Hydrolyzed Collagen) or mixed source (bovine, chicken, marine, eggshell—Wholesome Wellness Hydrolyzed Multi Collagen). The blended powders were then added to saline, mixed and left at room temperature for 5 minutes to form pseudoplastic scaffolds (Table 6).

TABLE 6

| | Part A | | | | Part B |
|---|---|---|---|---|---|
| Formula | Formula D Powder (g) | HC-bovine (g) | HC-marine (g) | HC-mixed (g) | Saline (g) |
| K | 0.1054 | 0.0067 | | | 1.80 |
| L | 0.1013 | | 0.0068 | | 1.80 |
| M | 0.1008 | | | 0.0071 | 1.80 |

Lyophilized Formulas K, L and M formed stationary hydrogels, which were shear thinning. Shear thinning was tested via vortexing while in a glass vial. The hydrogels thinned under shear but became stationary hydrogels when vortexing/shear stopped.

Example 6: Examples of Additives

Hydrolyzed collagen-bovine (0.336 g) and bovine limed bone gelatin 200 BL (0.503 g) were dissolved in DI water (10.015 g) at 70° C. The 2-arm PEG B (0.113 g) was dissolved in DI water (10.019 g) at room temperature. The PEG solution was blended with the gelatin/HC solution and reacted overnight at room temperature and then frozen at −80° C. The resulting PEGylated PHC-containing microgel mixture was lyophilized and then ground to form a white powder. The resulting PEGylated PHC-containing microgel powder is a molar ratio of 10 moles PEG:1 Gelatin: 10 HC. The PEGylated PHC-containing microgel powder's pH is 4.79 and it could absorb 18 times its weight in saline.

Representative additives were mixed into the HC/MG powder and then saline was added. Compositions and results are shown in Table 7.

TABLE 7

| | Additive (g) | HC/MG (g) | wt % additive in dry powder | Saline (g) | Results |
|---|---|---|---|---|---|
| Pullulan | 0.0002 | 0.0253 | 0.78% | 0.4562 | pseudoplastic gel |
| | 0.9907 | 0.0102 | 98.99 | 3.0299 | flowable gel |
| Micronized | 0.0002 | 0.0252 | 0.79 | 0.454 | pseudoplastic gel |
| SIS | 0.0992 | 0.001 | 99.00 | 1.5075 | pseudoplastic gel |
| Bioglass | 0.0002 | 0.0251 | 0.79 | 0.4541 | pseudoplastic gel |
| | 0.9905 | 0.0103 | 98.97 | 1.0097 | paste |
| PLA | 0.0002 | 0.0253 | 0.78 | 0.4553 | pseudoplastic gel |
| | 0.0995 | 0.0011 | 98.91 | 1.5148 | pseudoplastic gel |
| | | | wt % in gel | | |
| Lidocaine | 0.0097 | 0.0254 | 1.98% | 0.4545 | pseudoplastic gel |
| Aspirin | 0.0104 | 0.0254 | 2.13 | 0.4527 | pseudoplastic gel |
| Vitamin C | 0.0102 | 0.0252 | 2.08 | 0.454 | pseudoplastic gel |

Example 7: Molar Range of Hydrolyzed Collagen to Protein Component

Hydrolyzed collagen-bovine and bovine limed bone gelatin 200 BL were dissolved in DI water at 70° C. The 2-arm PEG B was dissolved in DI water at room temperature. The PEG solution was blended with the gelatin/HC solution and reacted overnight at room temperature and then frozen at −80° C. The resulting PEGylated PHC-containing microgel was lyophilized and then ground to form white powder.

The powder samples were evaluated for saline absorption. The inputs for each of the samples and the results of the saline absorption are provided below in Table 8.

TABLE 8

| | | | | Part A | | Part B | | | |
|---|---|---|---|---|---|---|---|---|---|
| | Molar Ratio | | | 2-Arm | Water | Gelatin | HC | Water | Saline |
| Composition | PEG | Gelatin | HC | Peg (g) | (g) | (g) | (g) | (g) | absorption |
| 1 | 10 | 1 | 10 | 0.1132 | 10.0185 | 0.5031 | 0.3360 | 10.0154 | 18 × solids weight |
| 2 | 10 | 1 | 20 | 0.1110 | 10.0094 | 0.5058 | 0.6669 | 10.0220 | 12× |
| 3 | 10 | 1 | 30 | 0.1120 | 10.0295 | 0.5058 | 1.0059 | 10.0103 | 10× |
| 4 | 10 | 1 | 40 | 0.1153 | 10.0189 | 0.5037 | 1.3317 | 10.0284 | 8× |
| 5 | 10 | 1 | 50 | 0.1162 | 10.0238 | 0.5044 | 1.6615 | 10.0057 | 6× |
| 6 | 2 | 1 | 10 | 0.045 | 10.025 | 1.001 | 0.668 | 10.028 | 16× (0.05 g in 0.80 mL) |
| 7 | 5 | 1 | 10 | 0.111 | 10.016 | 1.003 | 0.667 | 10.038 | 18× (0.05 g in 0.90 mL) |
| 8 | 10 | 1 | 10 | 0.222 | 10.034 | 1.002 | 0.667 | 10.015 | 20× (0.05 g in 1.00 mL) |

Samples 6, 7, and 8 were subsequently processed to make a gel and a film. Some relevant properties of the materials produced using samples 6, 7, and 8 are summarized below in Table 9.

TABLE 9

| Composition | Notes |
|---|---|
| 6 | Powder<br>Color: off-white<br>Saline Absorption: 16x (0.05 g in 0.80 mL)<br>Gel<br>Clear. Flowable when vortexed. Some insoluble particulates visible.<br>Film<br>Non-tacky film, opaque, creases when folded, breaks easily when pulled apart, tearable, breaks apart into smaller pieces when placed into water without agitation, small pieces swell in water |
| 7 | Powder<br>Color: off-white<br>Saline Absorption: 18x (0.05 g in 0.90 mL)<br>Gel<br>Clear. Flowable when vortexed. Some insoluble particulates visible.<br>Film<br>Non-tacky film, opaque, creases when folded, breaks easily when pulled apart, tearable, remains in one piece when placed into water without agitation, swells in water |
| 8 | Powder<br>Color: off-white<br>Saline Absorption: 20x (0.05 g in 1.00 mL)<br>Gel<br>Slightly opaque. Flowable when vortexed. Some insoluble particulates visible.<br>Film<br>Non-tacky film, opaque, creases when folded, breaks easily when pulled apart, tearable, remains in one piece when placed into water without agitation, swells in water, slightly more durable than 2:1:10 and 5:1:10. |

Example 8: Bovine Cartilage Explant Evaluation

Evaluations were conducted to determine the effects of hydrolyzed collagen on viable bovine cartilage explants. Three readouts were performed: cell viability (AlamarBlue), cytotoxicity (lactate dehydrogenase [LDH] assay), and extracellular matrix integrity (glycosaminoglycan [GAG] content in media). Viable bovine cartilage explants (purchased from Articular Engineering) were placed into a 96 well-plate. Explants were equilibrated in chondrocyte growth medium with 10% fetal bovine serum (FBS) overnight at 37° C. 5% $CO_2$. The medium was then removed and 200 μL of hydrolyzed collagen with microgel (approx. 30 mg/mL) in medium was added to the tissue samples. The hydrolyzed collagen with microgel composition was PEG: bovine gelatin:hydrolyzed collagen in 10:1:10 molar ratio. Control samples were treated with 200 μL of phosphate buffered saline (PBS). Tissue was incubated at 37° C., 5% $CO_2$ for the duration of the experiment and media refreshed every 2-3 days. On days 2, 5, and 7 media were collected for LDH and GAG analysis. Cell viability was evaluated using Alamar Blue assay. The data was normalized to total tissue weight or baseline signal where applicable.

Figure 4:
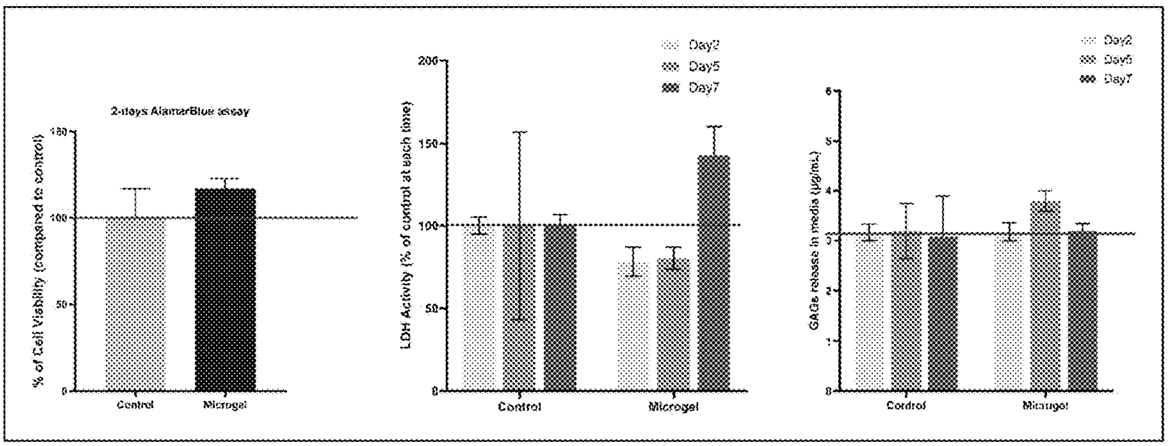
FIG. 4 shows percent cell viability, LDH activity, and glycosaminoglycan (GAG) content of treated cartilage explants with hydrolyzed collagen with microgel as compared to an untreated control.

Treatment of cartilage explants with hydrolyzed collagen with microgel resulted in approximately 15% higher cell viability, as determined on day 2 by Alamar Blue assay, compared to untreated control. The LDH activity, indicative of cell damage/lysis, was lower for the first two data points; more than 15% for both day 2 and day 5. The LDH activity increased on day 7 by approximately 40%, however, at this point, all of the formulation was replaced so it is likely additional treatment would result in a different outcome. The GAG analysis showed that the release of cartilage tissue matrix components over time parallels that of the control tissues, indicating no increase in matrix degradation with the treatment. All this data supports the findings of the hydrolyzed collagen with microgel formulation having a positive effect on cartilage tissue and improved cell and tissue viability compared to untreated control (FIG. 4).

While the above specification contains many specifics, these should not be construed as limitations on the scope of the invention, but rather as examples of preferred embodiments thereof. Many other variations are possible. Accordingly, the scope of this invention should be determined not by the embodiments illustrated, but by the appended claims and their legal equivalents.

What is claimed is:

1. A method of treating cartilage and peri-cartilage, comprising contacting cartilage and peri-cartilage with a pseudoplastic scaffold, wherein the pseudoplastic scaffold comprises:

a PEGylated protein-containing microgel, comprising a protein component crosslinked by a PEGylating component wherein the protein component comprises gelatin; and a hydrolyzed collagen component;

wherein the molar ratio of hydrolyzed collagen component to gelatin is 10:1.

2. The method of claim 1, wherein the contacting step comprises applying the pseudoplastic scaffold within cartilage or peri-cartilage.

3. The method of claim 1, wherein the composition is applied topically, via injection, or via ingestion.

4. The method of claim 1, wherein the contacting step comprises topical application of the pseudoplastic scaffold.

5. The method of claim 1, wherein the contacting step comprises injection into cartilage or peri-cartilage.

6. The method of claim 1, wherein the pseudoplastic scaffold is contacted with the cartilage and peri-cartilage in a form selected from a powder, a liquid, a gel, a paste, a cream, a suspension, an emulsion, a film, a sheet, a foam, a lotion, a spray, and an aerosol.

7. The method of claim 1, wherein the contacting step occurs during a surgical procedure.

8. The method of claim 1, wherein the pseudoplastic scaffold contains at least two times as much aqueous media as the dry pseudoplastic scaffold.

9. The method of claim 1, wherein the cartilage and peri-cartilage are impaired by at least one of inflammation, disease, a cut, a wound, a lesion, a fistula, a burn, a void, a surgical site, and a medical implant site.

10. The method of claim 1, wherein the pseudoplastic scaffold further comprises at least one biologic components selected from amniotic fluid, morselized amniotic tissue, exosomes, minced tissue, micronized tissue, micronized decellularized tissue, decellularized extracellular matrix derived from stem cells, granulated cross-linked bovine tendon collagen and glycosaminoglycans, cells and stem cells in cell culture medium, synthetic or naturally derived extracellular matrix components, including collagen, glycosaminoglycans, fibrin, laminin, and fibronectin, hydroxyapatite, honey, polysaccharides, biodegradable polymers, including polyglycolides, polylactides, poly(lactide-co-glycolide), polydioxanone, polycaprolactone, poly(trimethylene carbonate), poly(propylene fumarate), polyurethanes, poly(ester amide)s, poly(ortho ester)s, polyanhydrides, poly (amino acid)s, polyphosphazenes, and bacterial polysaccharides and proteins.

11. The method of claim 1, wherein the hydrolyzed collagen component is present during the reaction where the protein component is crosslinked by the PEGylating component, and wherein the PEGylated protein-containing microgel is a PEGylated PHC-containing microgel.

12. The method of claim 1, wherein the hydrolyzed collagen component is not crosslinked by the PEGylating component.

13. The method of claim 1, wherein a molar ratio of the PEGylating component to the protein component is at least 5:1.

14. The method of claim 1, wherein a molar ratio of the PEGylating component to the hydrolyzed collagen component is up to 1:1.

15. The method of claim 1, comprising 5 to 99 mole parts of the hydrolyzed collagen component; and 1 to 95 mole parts of the PEGylated protein-containing microgel.

16. The method of claim 1, comprising 8 to 82 mole parts of the hydrolyzed collagen component; and 18 to 92 mole parts of the PEGylated protein-containing microgel.

17. The method of claim 1, comprising 8 to 63 mole parts of the hydrolyzed collagen component; and 37 to 92 mole parts of the PEGylated protein-containing microgel.

18. The method of claim 1, wherein the pseudoplastic scaffold further comprises a biologically active agent selected from cells, stem cells, amniotic tissue, amniotic cells, exosomes, growth factors, decellularized extracellular matrix derived from stem cells, micronized decellularized tissue, granulated crosslinked bovine tendon collagen and glycosaminoglycans, antiprotozoal agents, sporicidal agents, antiparasitic agents, peripheral neuropathy agents, neuropathic agents, chemotactic agents, analgesic agents, anti-inflammatory agents, anti-allergic agents, anti-hypertension agents, mitomycin-type antibiotics, polyene antifungal agents, antiperspirant agents, decongestants, anti-kinetosis agents, central nervous system agents, wound healing agents, anti-VEGF agents, anti-tumor agents, escharotic agents, anti-psoriasis agents, anti-diabetic agents, anti-arthritis agents, anti-itching agents, antipruritic agents, anesthetic agents, anti-malarial agents, dermatological agents, anti-arrhythmic agents, anti-convulsants, antiemetic agents, anti-rheumatoid agents, anti-androgenic agents, anthracyclines, anti-smoking agents, anti-acne agents, anticholinergic agents, anti-aging agents, antihistamines, anti-parasitic agents, hemostatic agents, vasoconstrictors, vasodilators, thrombogenic agents, anti-clotting agents, cardiovascular agents, angina agents, erectile dysfunction agents, sex hormones, growth hormones, isoflavones, integrin binding sequences, biologically active ligands, cell attachment mediators, immunomodulators, tumor necrosis factor alpha, anti-cancer agents, anti-depressant agents, antitussive agents, anti-neoplastic agents, narcotic antagonists, anti-hypercholesterolemia agents, apoptosis-inducing agents, birth control agents, sunless tanning agents, emollients, alpha-hydroxyl acids, manuka honey, topical retinoids, hormones, tumor-specific antibodies, antisense oligonucleotides, small interfering RNA (siRNA), anti-VEGF RNA aptamer, nucleic acids, DNA, DNA fragments, DNA plasmids, Si-RNA, transfection agents, vitamins, essential oils, liposomes, exosomes, silver nanoparticles, gold nanoparticles, drug-containing nanoparticles, albumin-based nanoparticles, chitosan-containing nanoparticles, polysaccharide-based nanoparticles, dendrimer nanoparticles, phospholipid nanoparticles, iron oxide nanoparticles, bismuth nanoparticles, gadolinium nanoparticles, metallic nanoparticles, ceramic nanoparticles, silica-based nanoparticles, virus-based nanoparticles, virus-like nanoparticles, nitric oxide-containing nanoparticles, nanoshells, nanorods, polymeric micelles, quantum dots nanoparticles, polymer-based microparticles, polymer-based microspheres, drug-containing microparticles, drug-containing microspheres, salicylic acid, benzoyl peroxide, 5-fluorouracil, nicotinic acid, nitroglycerin, clonidine, estradiol, testosterone, nicotine, motion sickness agents, scopolamine, fentanyl, diclofenac, buprenorphine, bupivacaine, ketoprofen, opioids, cannabinoids, enzymes, enzyme inhibitors, proteins, prodrugs, protease inhibitors, hyaluronic acid, chondroitin sulfate, dermatan sulfate, para-sympatholytic agents, hair growth agents, lipids, glycolipids, glycoproteins, endocrine hormones, growth hormones, growth factors, differentiation factors, heat shock proteins, immunological response modifiers, saccharides, polysaccharides, insulin and insulin derivatives, steroids, corticosteroids, and non-steroidal anti-inflammatory drugs or similar materials, in either their salt form or their neutral form, either being inherently hydrophilic or encapsulated within a hydrophilic microparticle or nanoparticle.

19. The method of claim 1, wherein the pseudoplastic scaffold further comprises at least one of cells, stem cells, amniotic tissue, amniotic cells, exosomes, growth factors, micronized decellularized tissue, decellularized extracellular matrix derived from stem cells, granulated collagen, or glycosaminoglycans.

* * * * *